(12) United States Patent
Martin et al.

(10) Patent No.: US 8,452,378 B2
(45) Date of Patent: May 28, 2013

(54) METHOD FOR DETERMINING ATTENUATION VALUES FOR PET DATA OF A PATIENT

(75) Inventors: Diana Martin, Herzogenaurach (DE);
Günther Platsch, Röthenbach (DE);
Martin Requardt, Nürnberg (DE);
Sebastian Schmidt, Weisendorf (DE);
Kristin Schmiedehausen, Palo Alto, CA (US); Michael Szimtenings, Bonn (DE)

(73) Assignee: Siemens Aktiengesellschaft, Munich (DE)

( * ) Notice: Subject to any disclaimer, the term of this patent is extended or adjusted under 35 U.S.C. 154(b) by 944 days.

(21) Appl. No.: 12/232,522

(22) Filed: Sep. 18, 2008

(65) Prior Publication Data

US 2009/0105583 A1    Apr. 23, 2009

(30) Foreign Application Priority Data

Sep. 20, 2007    (DE) .......................... 10 2007 044 874

(51) Int. Cl.
*A61B 5/05*    (2006.01)
(52) U.S. Cl.
USPC ........... 600/427; 600/407; 600/410; 600/411; 600/436
(58) Field of Classification Search
USPC ................................ 600/407, 411, 427, 436
See application file for complete search history.

(56) References Cited

U.S. PATENT DOCUMENTS

2005/0253584 A1    11/2005    Campagna
2007/0100225 A1*    5/2007    Maschke ........................ 600/407

FOREIGN PATENT DOCUMENTS

| JP | 6308243 | 11/1994 |
|---|---|---|
| JP | 9152484 | 6/1997 |
| WO | WO 02/089902 | 11/2002 |
| WO | WO 2005/026748 | 3/2005 |
| WO | WO 2006/026402 | 3/2006 |
| WO | WO 2007/092696 | 8/2007 |

OTHER PUBLICATIONS

Habib Zaidi et al.; Magnetic resonance imaging-guided attenuation and scatter corrections in three-dimensional brain positron emission tomography; Med.Phys. 30 (5), May 2003, S. 937-948; Others.
J. Rahmer; P. Börnert; C. Bos; J. Groen; G. Mens; Tendon Imaging Using 3D Ultrashort TE Scanning; Proc. Intl. Soc. Mag. Reson. Med. 14 (2006), S. 1723; Others.
Office Action for corresponding German Application No. 10 2007 044 874.2-35 dated May 9, 2008.
Notification of Reasons for Refusal for corresponding Japanese patent application No. 2008-239517 dated Jun. 19, 2012 with English translation.

* cited by examiner

*Primary Examiner* — Unsu Jung
*Assistant Examiner* — Joel Lamprecht
(74) *Attorney, Agent, or Firm* — Harness, Dickey & Pierce, P.L.C.

(57) ABSTRACT

A method is disclosed for determining attenuation values for PET data of a patient. In at least one embodiment, the method includes detecting at least one accessory of a magnetic resonance imaging scanner and detecting the position and/or alignment of the accessory by way of an imaging measuring method; comparing the detected accessory with data from a database; and assigning an attenuation map, which is contained in the database, to attenuation values of the detected accessory and adapting the attenuation map to the detected position and/or alignment of the accessory.

18 Claims, 2 Drawing Sheets

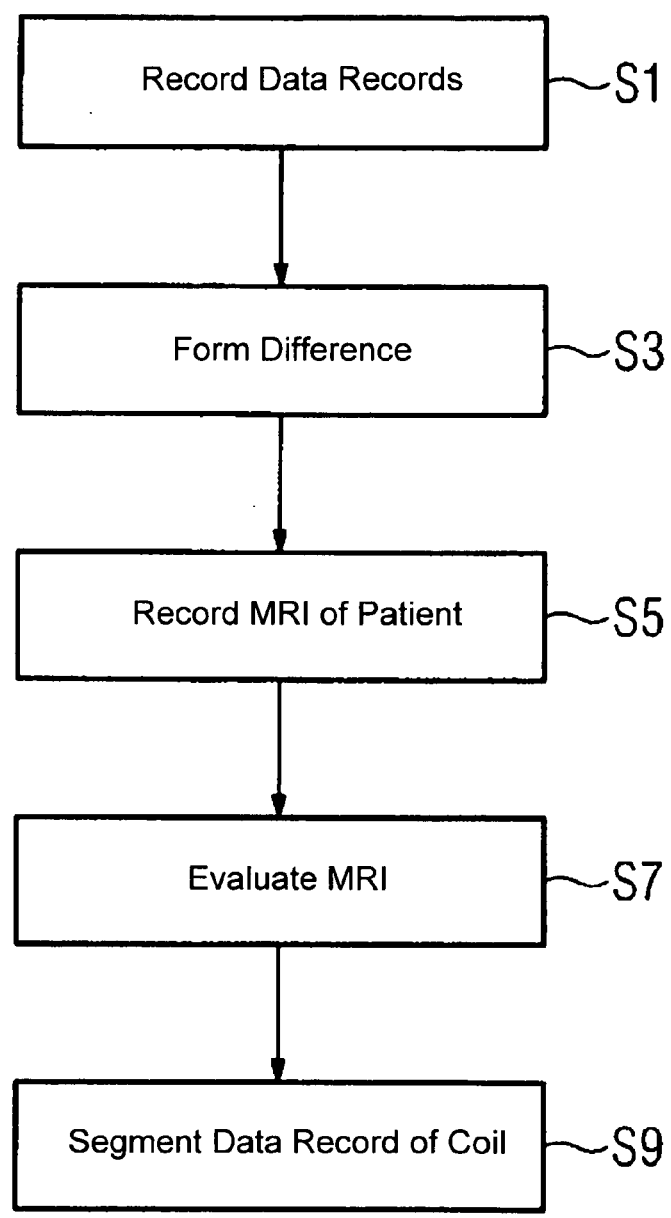

METHOD FOR DETERMINING ATTENUATION VALUES FOR PET DATA OF A PATIENT

PRIORITY STATEMENT

The present application hereby claims priority under 35 U.S.C. §119 on German patent application number DE 10 2007 044 874.2 filed Sep. 20, 2007, the entire contents of which is hereby incorporated herein by reference.

FIELD

Embodiments of the present invention generally relate to a method for determining attenuation values for PET data of a patient.

BACKGROUND

In recent years, the use of both positron emission tomography (PET) and magnetic resonance imaging (MRI) for medical diagnosis has become more widespread. While MRI is an imaging method for displaying structures and slice images in the interior of the body, PET allows visualizing and quantifying metabolic activities in vivo.

PET uses the particular properties of positron emitters and positron annihilation to quantitatively determine the function of organs or regions of cells. Appropriate radiopharmaceuticals marked with radionuclides are administered to the patient before the examination. When the radionuclides decay, they emit positrons which within a short distance interact with electrons, and this results in a so-called annihilation. This creates two photons which fly apart in opposite directions (offset by 180°). These photons are detected by two PET detector modules lying opposite to one another within a particular time frame (coincidence measurement), as a result of which the location of the annihilation is determined to be at a position along the connecting line between these two detector modules.

For the purpose of detection, the detector module in PET must in general cover a large portion of the gantry arc length. It is subdivided into detector elements with a side length of a few millimeters. Each detector element generates an event record if it detects a photon, specifying the time and detection location, that is to say the corresponding detector element. This information is transmitted to a fast logic and compared. If two events occur within a maximum period of time, a pair annihilation process is assumed to have occurred on the connecting line between the two corresponding detector elements. A tomography algorithm, that is to say the so-called back projection, is used to reconstruct the PET image.

Particularly when recording PET data in combined scanners (for example, MRI/PET scanners), there are moveable objects such as MR coils and supporting devices, and immovable objects such as the patient couch, between the patient to be examined and the PET detectors. In addition to attenuation of the PET signal by the tissue of the patient, which is always present and through which the annihilation radiation has to pass from its source location to the PET detector, the abovementioned objects also attenuate the PET signal. This leads to artifacts in the resultant PET images.

MRI scanners have so-called local coils which can be positioned on the body of the patient by the examiner to keep the distance to the source of the MRI signal as small as possible. While it is possible to a large extent to calculate the attenuation values of the patient tissue from the MRI data recorded in parallel with the PET data, this is not possible straight away for the abovementioned objects outside of the patient. The described problems have only occurred since the development of MRI/PET scanners because in this case work is undertaken with various objects in the beam path of the PET signal. The number of objects in the beam path of the MRI/PET scanner should in principle be kept as low as possible so as to minimize the influence of absorption and scattered radiation.

PET systems are known to be normalized such that on the one hand the differing sensitivities of the individual detector elements of the PET detection system are compensated for. On the other hand, it is possible to correct the influence of stationary objects since these are at the same location both during the normalization and during the later measurement of the patient. In principle it is possible to make such a correction for all objects used during a measurement. This is effected by a separate transmission measurement using a radioactive source or a PET/CT measurement. A map of attenuation values (μ-map) is determined from this transmission measurement. However, this data is of limited use in the actual measurement of a patient because, in particular, the position and alignment of moveable objects such as local coils change in each measurement.

WO 2007/092696 A2 discloses a method for assigning attenuation values to pixels of a CT image. A CT image is segmented and regions with different CT numbers are identified in the process. To be precise, regions with tissue, bone and foreign objects are differentiated. By applying a transformation prescription, the attenuation values can be directly determined from the data of the CT image. Only different coefficients for the various classes of material have to be taken into account. The coefficients for various materials are stored in a look-up table. The conversion prescription of CT images is designed such that each CT number can be assigned an attenuation value on the basis of the coefficient. Alternatively, it is possible that coefficients for objects comprising a number of materials are stored in the look-up table.

SUMMARY

In at least one embodiment of the present invention, a method is specified for determining attenuation values by which accessories of an imaging examination scanner can be taken into account.

According to at least one embodiment, a method for determining attenuation values for PET data of a patient comprises:
   detecting at least one accessory of a magnetic resonance imaging scanner and detecting the position and/or alignment of the accessory by way of an imaging measuring method,
   comparing the detected accessory with data from a database, and
   assigning an attenuation map, which is contained in the database, to attenuation values of the detected accessory and adapting the attenuation map to the detected position and/or alignment of the accessory.

By way of example, the specified method of at least one embodiment can be used before measuring PET data of the patient. If accessories are used in the measurement, these are detected by an imaging measuring method in the first method step in order to be identified. In the second and third method steps, attenuation values of the detected accessory are read out from a database and assigned to the accessory. The read-out attenuation values can be used for attenuation correction of the PET data.

As a result of this, it is possible to correct the attenuation of moveable (and fixed) accessories in each measurement; previously this had been impossible. Preferably, the determined attenuation values are combined with the independently determined attenuation values of the patient to form a μ-map, so that the overall attenuation of the photons can be calculated.

Detecting the position and alignment of the accessory and adapting the attenuation map to the detected position and/or alignment of the accessory provides a particularly efficient method because attenuation values of the accessories determined from transmission measurements are stored in the database, as explained above. In order to then respectively determine the attenuation values of the accessory in a measurement of PET data of the patient to be conducted, it is only necessary to adapt the already known attenuation values from the database to the present position and alignment of the accessory. The advantage of at least one embodiment of this method is that recording the accessory is eased and reduced to detecting the position and alignment of the accessory.

In an advantageous embodiment of the invention, the imaging measuring method is an MRI measuring method. Particularly in the case of MRI/PET scanners, detection of the accessories by way of an MRI method is advantageous since no further detection systems are required for the accessory. Alternatively, it is possible to detect the accessory by way of an optical imaging system.

If the accessory is a receiving coil of the MRI scanner, one advantageous embodiment of the invention comprises detecting the receiving coil by measuring a magnetic resonance image including the receiving coil. The position and alignment of the receiving coil results from the analyzed illumination profile of the receiving coil. Analyzing the illumination profile is a proven method for determining the position and alignment of receiving coils in MRI scanners; noting that US 2005/253584, the entire contents of which are incorporated herein by reference, discloses such a method.

In an alternative, advantageous embodiment of the invention, detecting the accessory comprises recording an image of the accessory. The position and alignment of the accessory are determined by correlation analysis with a reference image of the accessory. Such image comparison with previously recorded reference images of the accessory by way of graphical image processing is a simple alternative for determining the position and alignment of the accessory. This method is not limited to receiving coils, but can be used for any accessory, i.e. supporting device(s), for example.

In a further advantageous refinement of at least one embodiment of the invention, the accessory is unambiguously identified by at least three markings. These markings are detected and the position and alignment of the accessory are determined by analyzing the spatial position of the at least three markings. The position and alignment of the accessory in space can easily be determined by the design of the markings themselves or their relative positions to one another. In addition, it is possible to unambiguously identify the accessory by way of the design and the orientation of the markings. By way of example, the three markings can be arranged at different distances to one another on every accessory to be detected.

BRIEF DESCRIPTION OF THE DRAWINGS

Further advantages and refinements of the invention emerge from the example embodiments described below in conjunction with the figures, in which:

FIG. 2 shows a schematic flowchart of an example embodiment of the method.

DETAILED DESCRIPTION OF THE EXAMPLE EMBODIMENTS

Figure 1:
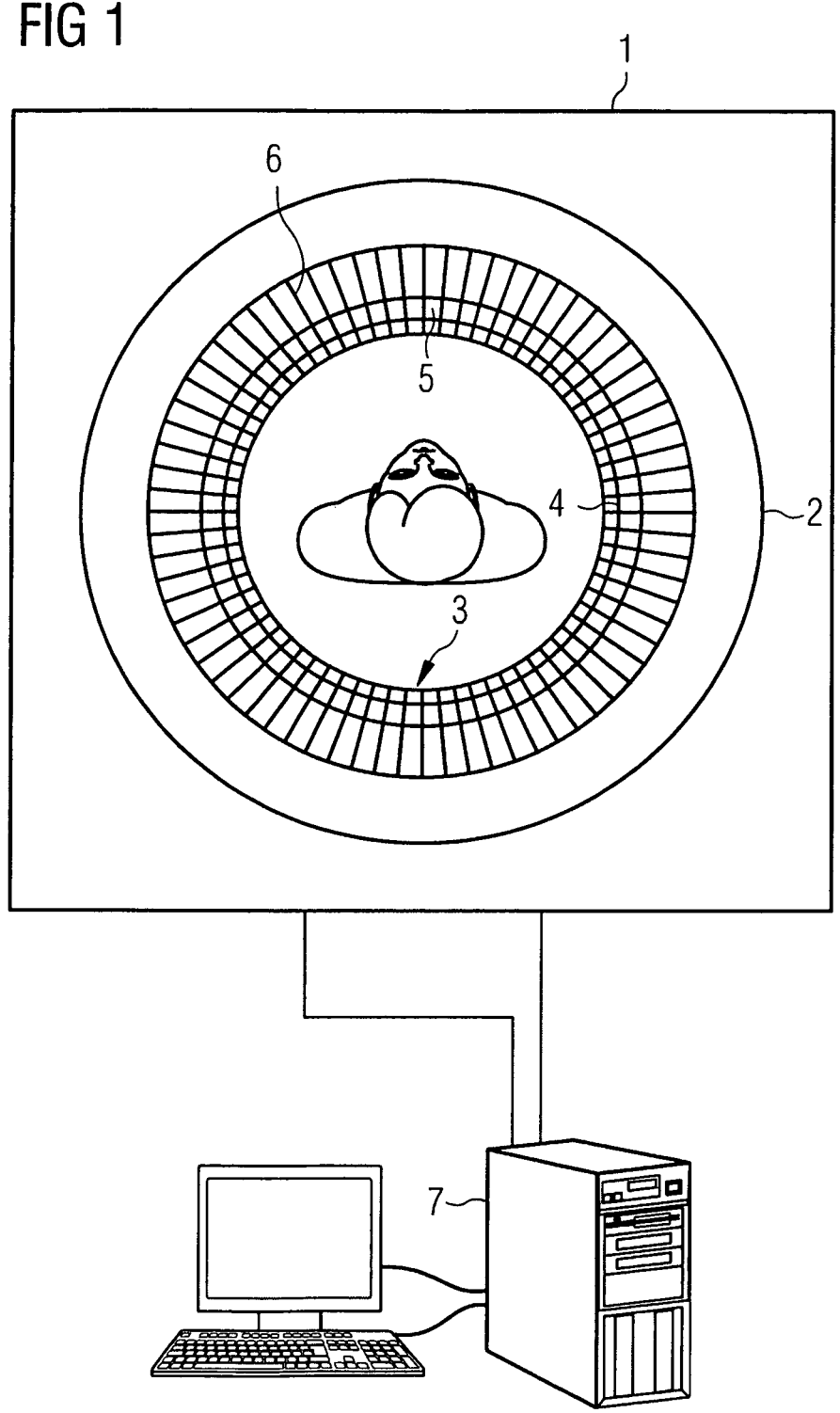
FIG. 1 shows a schematic illustration of a combined MRI/PET scanner.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The example embodiments of the invention can preferably be used in a combined MRI/PET scanner. The advantage of a combined scanner is that both MRI and PET data can be obtained isocentrically. This makes it possible to precisely define the examination volume within the region of interest using the data of the first modality (PET), and to use this information in the further modality (e.g. magnetic resonance). Although it is possible to transfer volume information of the region of interest from an external PET scanner to an MRI scanner, there is increased complexity in registering the data.

In general, all data determinable by magnetic resonance or other imaging methods can be established in the region of interest selected from the PET data record. By way of example, instead of obtaining spectroscopy data, it is also possible to obtain fMRI data, diffusion maps, T1 or T2 weighted images or quantitative parameter maps by way of magnetic resonance examinations in the region of interest. It is also possible to use methods from computed tomography (e.g. perfusion measurements, multi-energy imaging) or x-rays. The advantage of the described method in each case is that by way of the PET data record the region of interest can be limited in a very targeted manner to a specific pathology of the patient present.

However, it is also possible to additionally display various biological characteristics in the PET data record by using a number of so-called tracers and thus further optimize the region of interest and the fixed volume determined by this, or to simultaneously select a number of different examination volumes which are analyzed in subsequent examinations.

FIG. 1 shows a known apparatus 1 for superposed MRI and PET imaging. The apparatus 1 includes a known MRI tube 2. The MRI tube 2 defines a longitudinal direction z which extends orthogonally to the plane of the drawing of FIG. 1.

As shown in FIG. 1, a plurality of PET detection units 3 arranged in mutually opposing pairs around the longitudinal direction z are arranged coaxially within the MRI tube 2. The PET detection units 3 preferably comprise an APD photodiode array 5 with an upstream array of LSO crystals 4 and an electrical amplifying circuit (AMP) 6. However, embodiments of the invention are not limited to PET detection units 3 with the APD photodiode array 5 and the upstream array of LSO crystals 4; rather, differently designed photodiodes, crystals and apparatuses can similarly be used for detection.

The image processing for the superposed MRI and PET imaging is carried out by a computer 7.

The MRI tube 2 defines a cylindrical first field of view along its longitudinal direction z. The multiplicity of PET detection units 3 define a cylindrical second field of view along the longitudinal direction z. According to an embodiment of the invention, the second field of view of the PET detection units 3 substantially corresponds to the first field of view of the MRI tube 2. This is implemented by correspondingly adapting the arrangement density of the PET detection units 3 along the longitudinal direction z.

In general, it is usual to calculate an attenuation map ($\mu$-map) which corrects the attenuation of the photons by the patient. In this p-map, the attenuation value of the material present in each pixel is stored for each pixel. The attenuation values then are used for attenuation correction corresponding to the trajectory of the photons.

By way of the embodiments of the methods described in the following text, it is not only the patient but also present accessories used for the measurement which are taken into account when generating such p-maps. By way of example, these accessories could be the patient table, supporting device (s) and the receiving coils (local coils) of the MRI scanner which can be placed at different locations and are generally used. In any case, it is firstly necessary to measure the attenuation values of the individual accessories by way of transmission measurements of a radioactive source without a patient and use these to generate an attenuation map for the respective accessory. The attenuation maps of the measured objects are stored in a database.

What accessories are used for the measurement has to then be determined prior to each measurement. For example, the patient table is used in every measurement. However, in general, the position of the patient table will differ between two measurements. For example, this is the case if, in one measurement, the head of the patient is measured at the front end of the patient table, and in a subsequent measurement the abdomen of a patient is measured in the central part of the patient table. In general, the attenuation values of the patient table will differ depending on the position of the patient table. However, since the position of the patient table relative to the PET detection system is known from the coordinate system of the MRI/PET scanner, the correct attenuation value of the respective position of the patient table can be selected according to the previously determined attenuation map and can be used for attenuation correction.

In the case of accessories which can be moved freely relative to the MRI/PET scanner, for example supporting devices and receiving coils, the position and alignment of the respective accessory in the coordinate system of the MRI/PET scanner must be established for every measurement in addition to the attenuation map. As soon as position and alignment of the accessory are known, the attenuation maps from the database can be adapted to the respective position and alignment of the accessory. These values are then combined with the $\mu$-map of the patient and the fixedly installed objects to form an overall $\mu$-map.

In order to determine the position and alignment of accessories, a number of example embodiments will be described in the following text. Some of the example embodiments can be used universally for all possible types of accessory. Other example embodiments are provided specifically for determining the alignment and position of receiving coils.

In one example embodiment of the invention, a magnetic resonance image is recorded by a receiving coil whose position and alignment are intended to be detected. The illumination profile of the coil is determined in the process of evaluating the magnetic resonance image. The position and alignment of the coil can be calculated from this illumination profile, as known from US 2005/253584, the entire contents of which are hereby incorporated herein by reference.

In an alternative example embodiment of the invention, an image of the housing of the accessory is recorded by way of an MRI sequence having very short echo times (e.g. UTE, disclosed in WO 2006/26402 and WO 2005/026748, the entire contents of each of which are hereby incorporated herein by reference). The position and alignment of the coil can be calculated in the recorded MR image by way of image processing methods. On the one hand, it is possible to determine the position and alignment of the coil by correlation analysis with a reference image of the corresponding coil. A rotation matrix and a translation vector are determined in the process. They determine a rotation and translation of the coil's reference image which superposes the reference image of the coil onto the currently recorded image. Methods to calculate this transformation are known under the term of rigid image registration.

On the other hand, it is possible to segment the recorded MR image without using a reference image. Segmenting the image of the coil separates it into various regions of different materials, the attenuation coefficients of which are stored in the database. In this, manner it is possible to flexibly readout attenuation maps of the accessories from the database and incorporate the attenuation values in the μ-map.

In a further alternative example embodiment, the accessories are provided with at least three punctiform markings which can be detected easily and automatically in the MR image. All substances exhibiting a strong contrast behavior in the MR image are suitable marking substances. Examples of this include iron, fluorine, gadolinium and the like. The position of these three points in space is measured at the beginning of the examination by way of an MRI measurement. If the position of a receiving coil of the MRI scanner is intended to be determined, the type of the receiving coil used is known to the software of the MRI scanner.

This information is required to operate the receiving coil and is generally automatically detected as soon as electrical contact is made between the receiving coil and the MRI scanner. In this respect, it is possible for the corresponding software of the MRI scanner to assign from the database the corresponding attenuation map for the receiving coil used. This attenuation map can be rotated accordingly by using the position and alignment which were determined by the position of the three markings in space, and can be inserted into the μ-map.

If other accessories are also intended to be identified by way of markings, the markings can be used for unambiguous identification. By way of example, it is possible that the type of accessory is encoded into the markings. This can be effected, for example, by different spacings of the markings or individual shaping.

In a further alternative, barcodes or RFID tags are used to identify the accessory. An appropriate scanner has to be attached to the measuring unit to read out the barcode or RFID tag.

FIG. 2 illustrates a schematic flowchart of an example embodiment of the invention. Using the example of a receiving coil attached to the patient, it is intended to show how an attenuation map of the patient and the receiving coil can be calculated. In a method step S1, two 3D data records having two different echo times are recorded with the aid of the UTE MRI sequence. The method is described in J. Rahmer et al.; "Tendon Imaging Using 3D Ultrashort TE Scanning"; Proc. Intl. Soc. Mag. Reson. Med. 14 (2006), the entire contents of which are hereby incorporated herein by reference.

The receiving coil attached to the patient can be recognized in both 3D data records. To improve the illustration, the difference of the two 3D data records is formed in a second method step S3. This yields an image resulting from only the signal of the protons with very short relaxation times.

In order to determine the attenuation values of the patient, an MRI data record of the patient is recorded in a third method step S5. This MRI data record is evaluated in a fourth method step S7 according to known methods (cf. H. Zaidi, et al.; "Magnetic resonance imaging-guided attenuation and scatter corrections in three-dimensional brain positron emission tomography"; Med. Phys. 30.5, May 2003, the entire contents of which are hereby incorporated herein by reference), so that this yields attenuation values of the patient tissue. The attenuation values are recorded in a μ-map of the patient. In a fifth method step S9, the 3D data record of the coil is segmented. As a result of this, it is possible to identify the receiving coil in the 3D data record. The UTE difference image only comprises the signal of the patient and the coil. Since the patient position was already determined in method step S7, all further signals can be assigned to the coil.

Since it is known which coils are used during the examination, the appropriate attenuation values of the segmented coil can be assigned to the corresponding pixels from segmenting. The receiving coil and the patient can be differentiated in the 3D data record on the one hand by the different signal intensities, and on the other hand by the generally known positions of receiving coil and patient. In a sixth method step S11, the attenuation values of the receiving coil are added to the μ-map of the patient. In a seventh method step S13, the μ-map determined in this way is used for attenuation correction of a recorded PET data record using known methods.

The method step S7 of determining the μ-map of the patient from the MRI data is substantially independent of determining the attenuation values of the receiving coil and can thus be inserted at a different position in the above-described method.

The described method is not limited to detecting the position and alignment of coils. Rather, this method makes it possible to correct the attenuation of other objects, such as supporting device(s) or headphones.

In an alternative embodiment of the invention, the position of the coils or other objects is determined in the fifth method step S9 by comparing them to reference images and by graphical analysis. In the process, it is likewise possible to conduct correlation analysis with reference images.

In a further alternative embodiment, the position of receiving coils is determined by analyzing the sensitivity profile of the receiving coil in an MR overview image recorded by this coil. It is only possible to determine receiving coils using this embodiment. In this case, it is possible to determine additional supporting device(s) or other objects using the previously specified methods, i.e. by segmenting these objects, for example.

The described methods are not limited to MRI/PET scanners. In principle it is also correspondingly possible to detect objects using other imaging scanners which are used together with PET and where attenuating objects are located in the beam path. For this purpose, methods appropriately suited to the modality used are to be used for determining the position and alignment of the objects.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining attenuation values from MR data of a patient in order to map to PET data of the patient, comprising:
    detecting at least one accessory of a magnetic resonance imaging scanner and detecting a change of at least one of a position and alignment of the at least one accessory via imaging measuring, the detected at least one accessory being an accessory of an imaging examination scanner which is not stationary relative to the imaging examination scanner;
    comparing the detected at least one accessory with data from a database;
    assigning attenuation values of the at least one detected accessory to an attenuation map, contained in the database, and adapting the attenuation map based on the detected change of at least one of position and alignment of the at least one accessory, the assigned attenuation values being first attenuation values;
    assigning second attenuation values from the database to accessories stationary relative to the imaging examination scanner;
    obtaining the MR data of the patient and third attenuation values associated with the MR data;
    combining the first, second and third attenuation values into a map of attenuation values of the patient; and
    applying the map of attenuation values of the patient to the PET data.

2. The method as claimed in claim 1, wherein the imaging measuring is magnetic resonance.

3. The method as claimed in claim 2, wherein the at least one accessory is a receiving coil and the method comprises:
    detecting the receiving coil by measuring a magnetic resonance image including the receiving coil and analyzing the illumination profile of the receiving coil, from which at least one of the position and alignment of the receiving coil results.

4. The method as claimed in claim 3, wherein the detecting of the at least one accessory includes recording an image of the at least one accessory, and wherein at least one of the position and alignment of the at least one accessory are determined by correlation with a reference image of the at least one accessory.

5. The method as claimed in claim 3, wherein the detecting of the at least one accessory includes recording an image of the at least one accessory, and wherein at least one of the position and alignment of the at least one accessory is determined by segmenting the image of the at least one accessory.

6. The method as claimed in claim 3, wherein the at least one accessory is detected by detecting at least three markings which identify the at least one accessory, and wherein at least one of the position and alignment of the at least one accessory are determined by analyzing the spatial position of the at least three markings.

7. The method as claimed in claim 2, wherein the detecting of the at least one accessory includes recording an image of the at least one accessory, and wherein at least one of the position and alignment of the at least one accessory are determined by correlation with a reference image of the at least one accessory.

8. The method as claimed in claim 2, wherein the detecting of the at least one accessory includes recording an image of the at least one accessory, and wherein at least one of the position and alignment of the at least one accessory is determined by segmenting the image of the at least one accessory.

9. The method as claimed in claim 2, wherein the at least one accessory is detected by detecting at least three markings which identify the at least one accessory and wherein at least one of the position and alignment of the at least one accessory are determined by analyzing the spatial position of the at least three markings.

10. The method as claimed in claim 1, wherein the detecting of the at least one accessory includes recording an image of the at least one accessory, and wherein at least one of the position and alignment of the at least one accessory are determined by correlation with a reference image of the at least one accessory.

11. The method as claimed in claim 1, wherein the detecting of the at least one accessory includes recording an image of the at least one accessory, and wherein at least one of the position and alignment of the at least one accessory is determined by segmenting the image of the at least one accessory.

12. The method as claimed in claim 1, wherein the at least one accessory is detected by detecting at least three markings which identify the at least one accessory, and wherein at least one of the position and alignment of the at least one accessory are determined by analyzing the spatial position of the at least three markings.

13. The method as claimed in claim 12, wherein the at least three markings are designed as a barcode.

14. The method as claimed in claim 12, wherein the at least three markings are designed as RFID tags.

15. The method as claimed in claim 1, in which the stationary accessory is a patient couch.

16. The method as claimed in claim 1, further comprising:
   recording a data record of the patient using the imaging examination scanner;
   calculating third attenuation values from data of the data record; and
   adding the third attenuation values to the map of attenuation values of the patient.

17. A non-transitory computer readable medium including program segments for, when executed on a computer device, causing the computer device to implement the method of claim 1.

18. An apparatus for determining attenuation values from MR data of a patient in order to map to PET data of the patient, the apparatus comprising:
   a computer configured to,
      detect at least one accessory of a magnetic resonance imaging scanner and detect a change of at least one of a position and alignment of the at least one accessory, the detected at least one accessory being an accessory of an imaging examination scanner which is not stationary relative to the imaging examination scanner,
      compare the detected at least one accessory with data from a database,
      assign attenuation values of the at least one detected accessory to an attenuation map, contained in the database, and adapt the attenuation map based on the detected change of at least one of position and alignment of the at least one accessory, the assigned attenuation values being first attenuation values,
      assign second attenuation values from the database to accessories stationary relative to the imaging examination scanner,
      obtain the MR data of the patient and third attenuation values associated with the MR data,
      combine the first, second and third attenuation values into a map of attenuation values of the patient, and
      apply the map of attenuation values of the patient to the PET data.

* * * * *